United States Patent [19]
Sakai et al.

[11] Patent Number: 5,192,692
[45] Date of Patent: Mar. 9, 1993

[54] METHOD OF JUDGING PARTICLE AGGLUTINATION PATTERN

[75] Inventors: Ko Sakai, Pt. Jefferson Sta.; Hiroyuki Yonekawa, St. James, both of N.Y.

[73] Assignee: Olympus Optical Co., Ltd., Japan

[21] Appl. No.: 384,497

[22] Filed: Jul. 25, 1989

[51] Int. Cl.$^5$ .......................................... G01N 15/04
[52] U.S. Cl. .................................. 436/165; 422/73; 364/497; 436/518; 436/519; 436/534; 436/805
[58] Field of Search ................... 436/43, 69, 164, 165, 436/518, 519, 520, 533, 534, 805, 807, 808, 809, 810; 422/73, 102; 73/64.1; 364/413.08, 497, 555

[56] References Cited

U.S. PATENT DOCUMENTS

| | | | |
|---|---|---|---|
| 4,447,396 | 5/1984 | Kano | 422/73 |
| 4,452,759 | 6/1984 | Takekawa | 422/73 |
| 4,452,902 | 6/1984 | Suovaniemi et al. | 422/73 X |
| 4,556,641 | 12/1985 | Kano et al. | 436/165 |
| 4,563,430 | 1/1986 | Kano et al. | 436/805 X |
| 4,580,895 | 4/1986 | Patel | 422/73 X |
| 4,661,460 | 4/1987 | Sakuma | 436/165 |
| 4,727,033 | 2/1988 | Hijikata et al. | 436/69 |
| 4,873,633 | 10/1989 | Mezei et al. | 422/73 X |

Primary Examiner—Robert J. Hill, Jr.
Attorney, Agent, or Firm—Parkhurst, Wendel & Rossi

[57] ABSTRACT

Particle patterns formed on a conical bottom surface of wells formed in a microplate are photoelectrically detected to produce a two-dimensional image signal, and then the two-dimensional image signal is processed to judge or classify the particle patterns as agglutinated patterns, non-agglutinated patterns or uncertain patterns with the aid of the two-dimensional image processing. An image signal representing a particle pattern is first extracted, and then the true or typical agglutinated and non-agglutinated patterns are judged by means of at least two fast judgments. When the pattern is not definitely judged, the image signal of the relevant pattern is further subjected to at least two precise judgments. When the pattern is judged to be the agglutinated pattern by the precise judgments, the relevant pattern is finally judged to be the true agglutinated pattern.

10 Claims, 12 Drawing Sheets

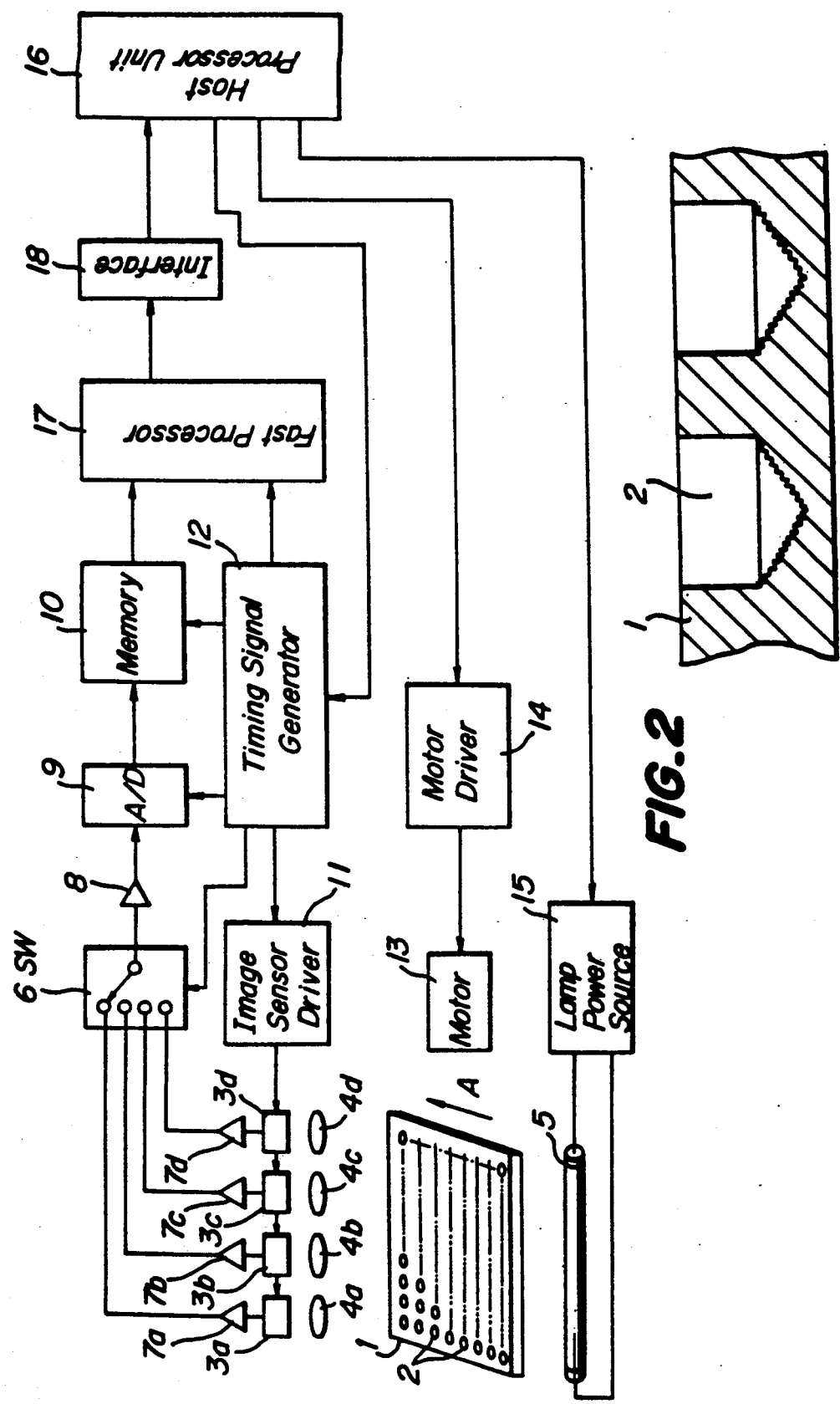

FIG. 4A

For Left Edge

| -1 | -1 | 0 | 1 | 1 |
|----|----|---|---|---|
| -1 | -1 | 0 | 1 | 1 |
| -1 | -1 | 0 | 1 | 1 |

FIG. 4B

For Right Edge

| 1 | 1 | 0 | -1 | -1 |
|---|---|---|----|----|
| 1 | 1 | 0 | -1 | -1 |
| 1 | 1 | 0 | -1 | -1 |

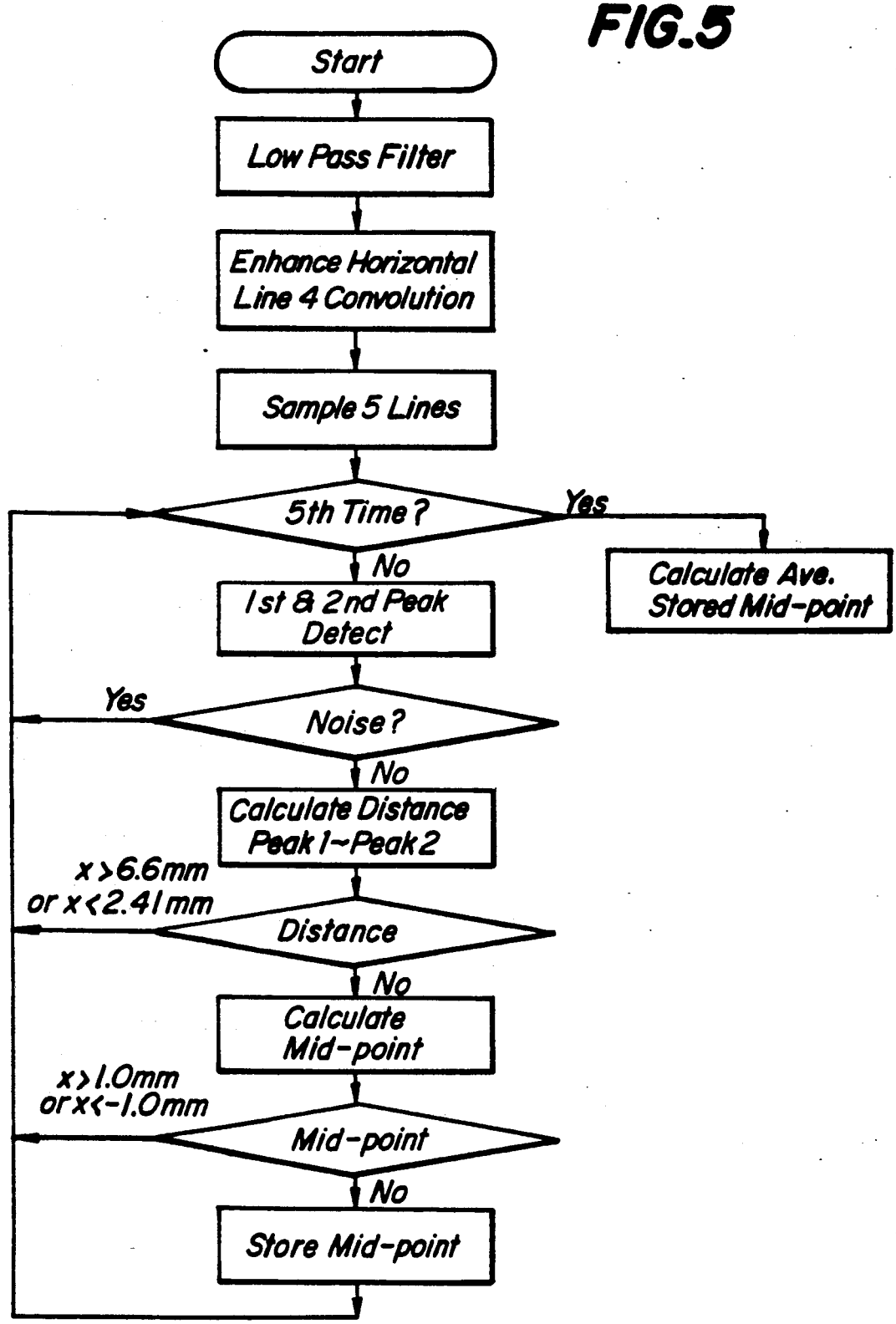

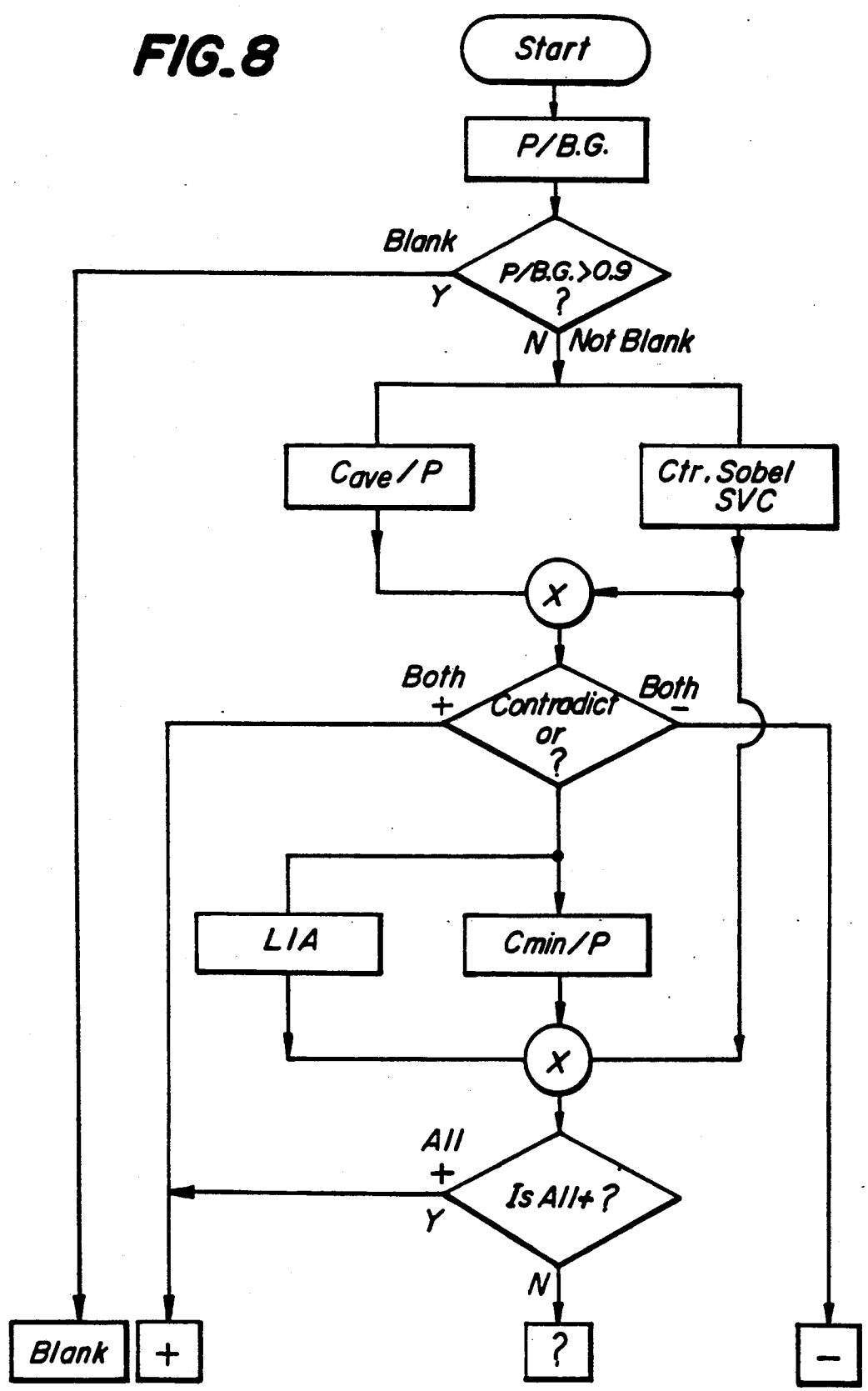

| 1 | 0 | -1 |
|---|---|----|
| 2 | 0 | -2 |
| 1 | 0 | -1 |

| 1 | 2 | 1 |
|---|---|---|
| 0 | 0 | 0 |
| -1 | -2 | -1 |

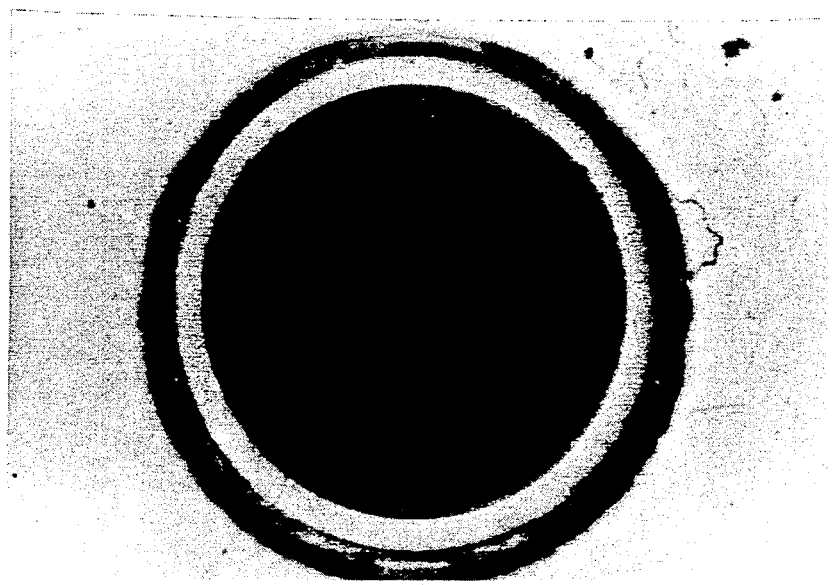
FIG_12A
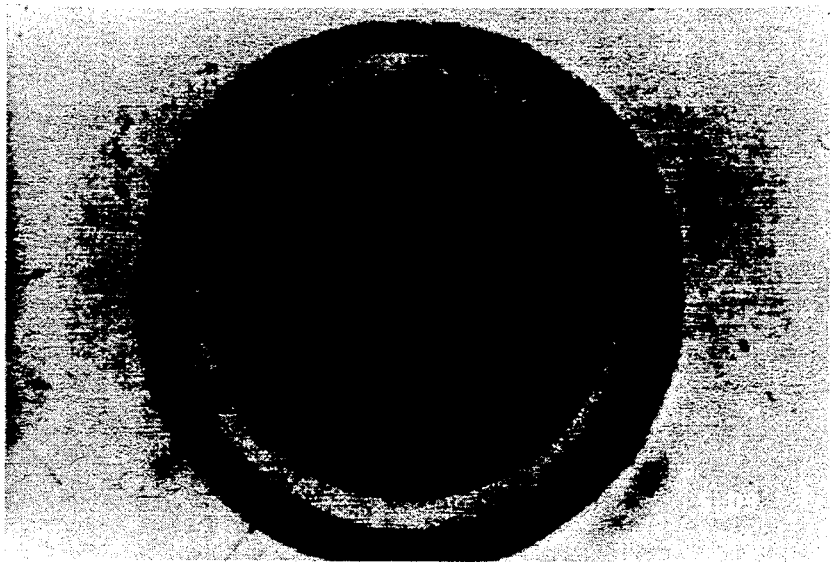
FIG_12B
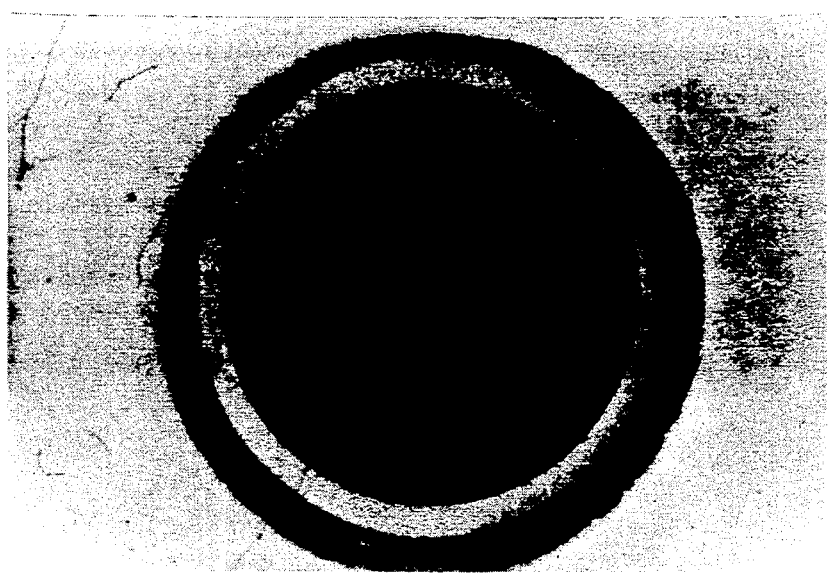
FIG_12C

FIG._12D
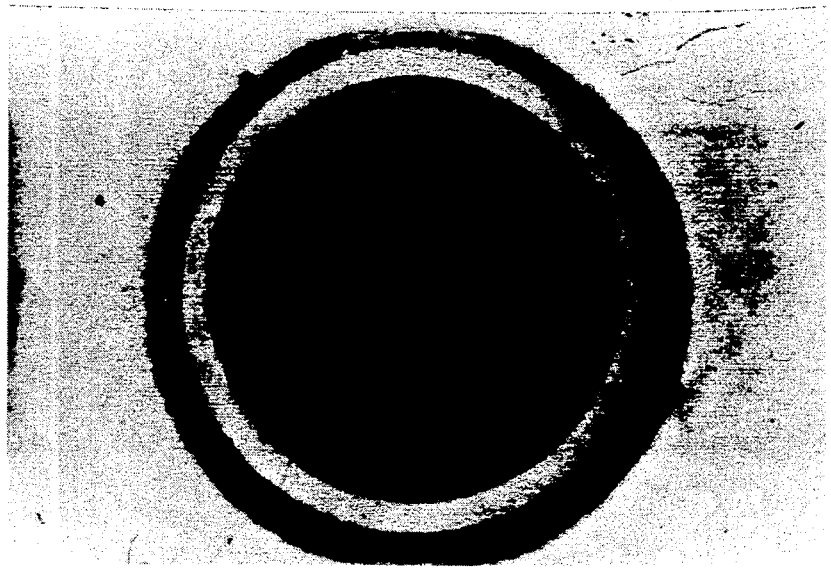
FIG._12E
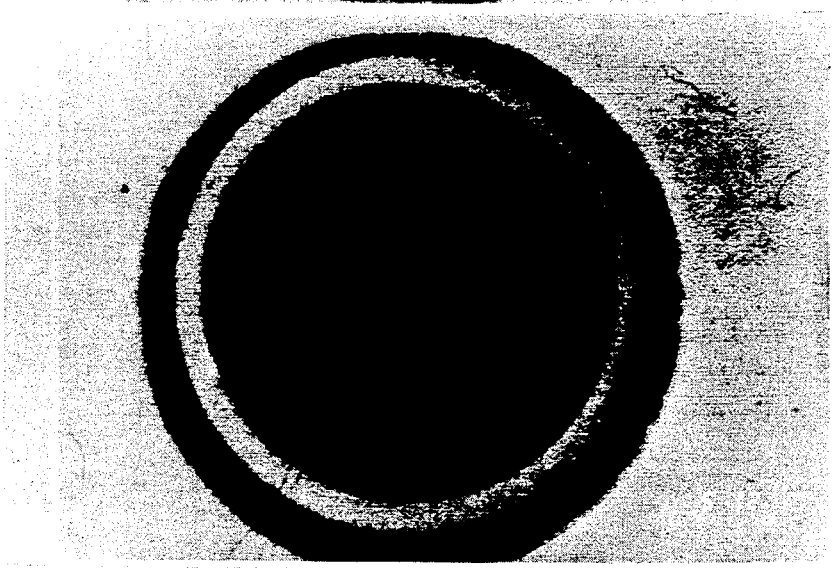
FIG._12F
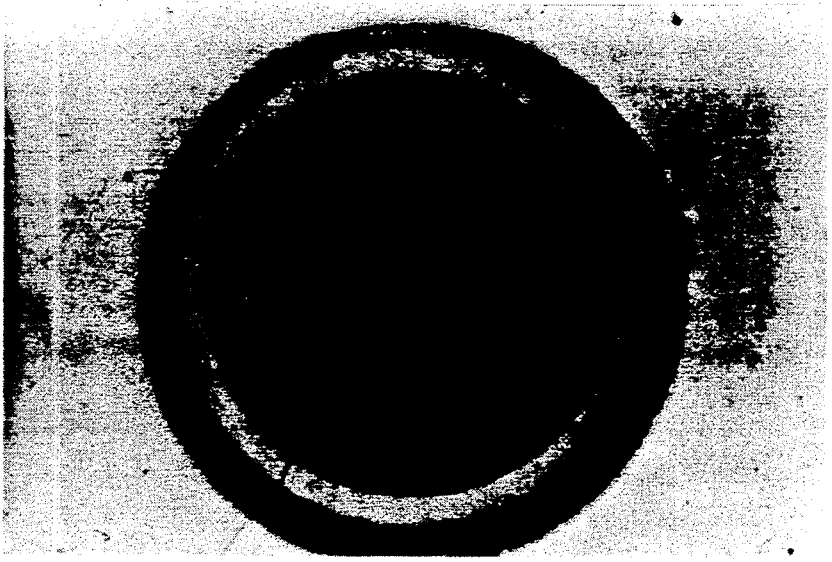

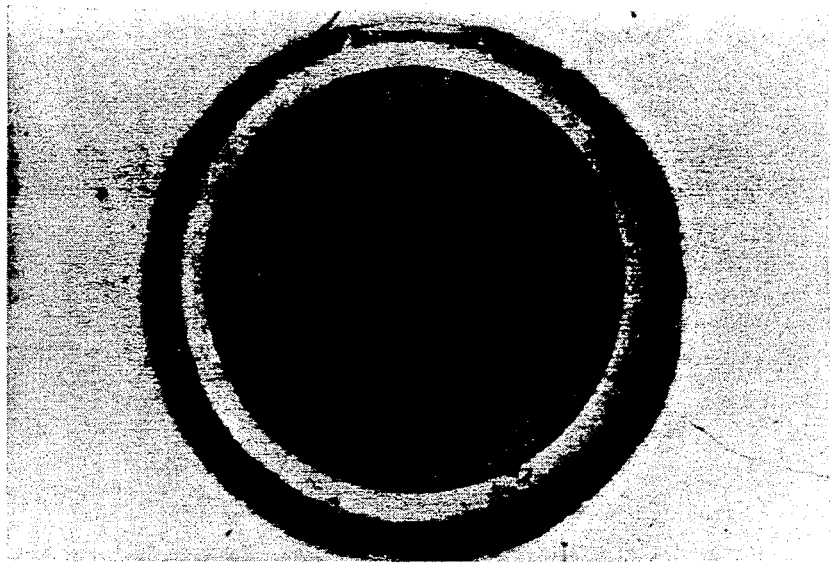
FIG_12G
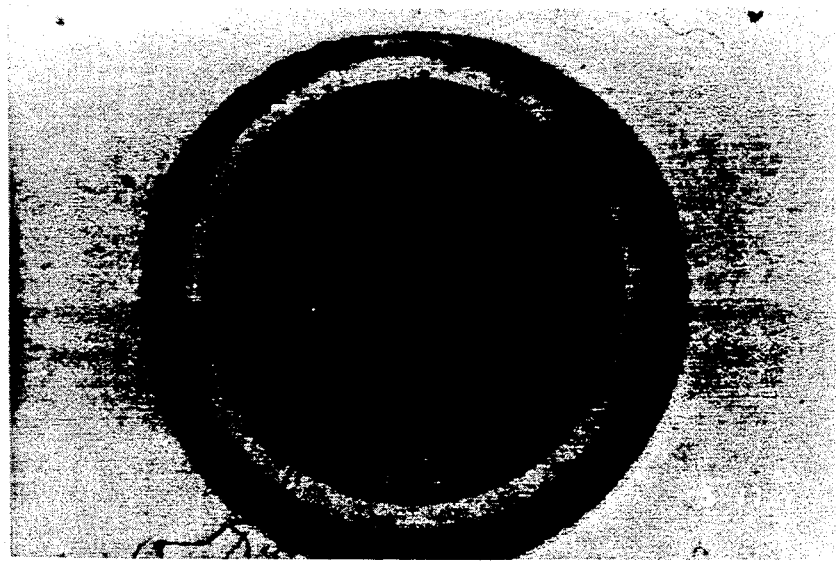
FIG_12H

METHOD OF JUDGING PARTICLE AGGLUTINATION PATTERN

BACKGROUND OF THE INVENTION

Field of the Invention and Related Art Statement

The present invention relates to a method of detecting and judging a particle agglutination pattern for use in diagnosis.

There has been developed an apparatus for analyzing a blood sample by detecting a particle agglutination pattern formed on a reaction vessel having an inclined bottom surface. Such an apparatus is described in, for instance U.S. Pat. No. 4,727,033 issued to K. Hijikata et al on Feb. 23, 1988. In this apparatus, a test liquid is formed in a conical reaction vessel by supplying a blood sample, i.e. blood cell sample or serum sample and a reagent, i.e. serum reagent or sensitized particle reagent into the reaction vessel, and then the reaction vessel containing the test liquid is kept still for a predetermined reaction time such as thirty minutes. During the reaction time, particles in the test liquid descend onto the inclined bottom surface. When the particles are agglutinated with each other, there is formed a uniformly agglutinated layer of the particles on the bottom surface, but when the particles are not agglutinated with each other, the particles roll down along the inclined bottom surface and are collected at the lowest bottom center to form a center dot. Then, the particle pattern formed on the bottom surface of the reaction vessel is photoelectrically detected by projecting light from one side of the reaction vessel and light transmitted through the reaction vessel is received by a photodetector. In FIG. 10 of the above mentioned U.S. Pat. No. 4,727,033, there is disclosed a photodetector having two concentrical light receiving regions, one for receiving light passing through a central portion of the reaction vessel and the other for receiving light transmitted through a peripheral portion of the reaction vessel. By processing output signals supplied from these light receiving regions, it is possible to judge whether the particle pattern is of the agglutinated pattern or non-agglutinated pattern. That is to say, when the particles are agglutinated with each other, there is not a significant difference between the output signals from the two light receiving regions, but when the non-agglutinated particle pattern is formed, the light passing through the central portion of the reaction vessel becomes weaker than the light transmitted through the peripheral portion, so that there is produced a large difference between the output signals supplied from the two light receiving regions. Therefore, by deriving a ratio of the output signal from the central light receiving region to the output signal from the peripheral light receiving region and comparing the ratio with predetermined upper and lower thresholds, the particle pattern formed on the inclined bottom surface can be judged and the sample blood can be analyzed. That is to say, when the ratio is greater than the upper threshold value, it is judged that the agglutination occurs, and when the ratio is smaller than the lower threshold value, it is judged that the agglutination does not occur. When the measured ratio is within the upper and lower threshold values, it is judged that the particle patter could not be judged certainly. It has been experimentally confirmed that the known method of judging the particle patter is suitable for judging true or typical particle patterns. However, in the actual analysis there are sometimes produced particle patterns which could no be judged definitely by the known method. In such a case, there is generated an automatic analysis result representing that the relevant sample could not be determined definitely, so that the sample has to be analyzed visually with naked eyes or has to be tested again. It has been found that the known method has the reexamination rate of about 20%. That is to say, when a hundred samples are tested, about twenty samples have to be subjected to the examination. In order to increase the efficiency of the analysis, it is desired to reduce the number of samples which should be analyzed again. In the known method, this may be effected by changing the threshold values for use in the comparison. However, then the accuracy of the analysis would be reduced, and the agglutinated pattern might be judged as the non-agglutinated pattern and the non-agglutination pattern might be judged as the agglutination pattern. Such an erroneous judgment would result in a serious problem and should be avoided particularly in the blood transportation. In case of analyzing infectious diseases, i.e. in case of detecting whether or not a sample is infected by various kinds of antigens such as Hb antigens including HBsAg, HBsAb, HBcAg, HBcAb, HBeAg and HBeAb, ATLA, HIV-(AIDS) and CMV, it would be necessary to enhance the sensitivity of agglutination, because the agglutinating force of these antigens is very weak. To this end, an amount of the reagent has to be made large, carriers of reagents have to be light in weight and the reaction time has to be made longer. Then, the non-agglutinated particles do not roll down along the inclined bottom surface promptly and the non-agglutinated particle pattern in which a large amount of particles are collected in the lowest central portion of the reaction vessel could not be formed correctly, so that the non-agglutinated pattern might be judged as the agglutinated pattern. Further, the cost of analysis is liable to increase remarkably and the efficiency of analysis becomes low to a great extent. In order to reduce the analyzing cost and time, an amount of the reagent has to be decreased and reagent carriers having heavy weight have to be used. In order to avoid such a problem, the threshold values have to be set such that particle patterns which could not be definitely judged are classified into an uncertain group and samples producing such uncertained particle patterns are analyzed visually with naked eyes or tested again with a different method, i.e. manual operation. In this manner, in the known agglutination analyzing method, the above mentioned contracting problems could not be solved. The above mentioned problems equally occur in the blood type analysis such as ABO, Rh and ABS (irregular antigen screening).

Further, in case of analyzing the above mentioned antigens having the weak agglutination force, such abnormal conditions have been sometimes experienced that a part of the uniformly deposited particle pattern is peeled from the bottom surface of the reaction vessel, and the center dot of the deposited particle pattern becomes small in size, unclear in sharpness or donut-like in shape. Then, the agglutinated particle pattern might be erroneously judged as the non-agglutinated pattern. This might also cause serious problems.

SUMMARY OF THE INVENTION

The present invention has for its object to provide a novel and useful method of detecting and judging a particle pattern formed on an inclined bottom surface of a reaction vessel in a reliable and economical manner, while the number of samples which have to be analyzed visually with naked eyes or tested again with a different method can be reduced remarkably without decreasing the accuracy of the analysis.

It is another object of the invention to provide a particle pattern detecting and judging method in which a particle pattern can be precisely judged even if the particle pattern has the above-stated abnormal conditions, i.e. a part of the uniformly agglutinated pattern is peeled off the bottom surface of the reaction vessel, etc.

According to the invention, a method of judging a particle pattern formed on an inclined bottom surface of a reaction vessel, comprises the steps of:

photoelectrically scanning the particle pattern to derive an image signal representing a two-dimensional image including the whole particle pattern;

processing the image signal of the two-dimensional image to derive a position signal representing the position of the bottom surface of the reaction vessel in the two-dimensional image;

processing said image signal of the two-dimensional image on the basis of said position signal to derive at least two characteristics of the particle pattern; and judging the particle pattern on the basis of said at least two characteristics.

In the method according to the invention, at first the position signal representing the center of the particle pattern is detected In case of using a microplate having a number of wells formed therein in matrix, the position signal can be derived by detecting an edge of the well which defines a boundary between a periphery of the well and a top surface of the microplate. According to the present invention, since the position signal can be detected by processing the two-dimensional image signal, it is no longer necessary to position the microplate very precisely with respect to the photoelectric detecting system. Therefore, the mechanism for transporting the microplate through the photoelectric detector can be made simple and cheap. Then, at least two characteristics of the two-dimensional particle pattern image are derived by utilizing the well-developed image processing technique. As will be explained in detail with reference to a preferable embodiment, in order to make the efficiency of the judgment high, it is desired to use initially high speed screening to discriminate typical agglutination pattern and non-agglutination pattern from other patterns, and then the remaining patterns are judged by using a secondary precise judgment. The high speed screening may be carried out by using a ratio of the density of the lowest central portion of the bottom of the reaction vessel to the density of the peripheral portion of the bottom and by using the sharpness of the center dot. In this manner, according to the invention, the particle pattern is judged by utilizing the two-dimensional image processing and thus the judgment can be performed in an accurate manner and the number of samples which have to be subjected to the visual inspection and/or reexamination can be reduced remarkably.

The inventors of the instant application have experimentally found that the typical or true non-agglutinated pattern has the following characteristics:

(1) A large number of particles are collected at the center of the inclined bottom surface to form the clear central dot having a high density.

(2) There is formed a sharp boundary between the central dot and the peripheral portion surrounding the central dot.

(3) The density of the peripheral portion is low.

The true or typical agglutinated pattern has the following characteristics:

(1) The central portion and peripheral portion have substantially the same density, but the density in the central portion is slightly higher than that in the peripheral portion.

(2) The peripheral portion has a uniform density.

(3) The number of particles collected at the center of the bottom surface is small.

In the visual judgment, the above mentioned characteristics of the particle patterns are selectively detected and the final judgment is provided by the combination of plural results of various judgments. According to the present invention, the particle patterns are judged in a similar manner to the above visual inspection, so that the particle patterns can be judged accurately and reliably as if they are judged by an operator with experienced eyes. Therefore, the possibility of the erroneous judgment and the number of samples which have to be analyzed again can be reduced to a great extent.

BRIEF DESCRIPTION OF THE DRAWINGS

FIG. 1 is a block diagram showing an apparatus for carrying out the method according to the invention;

FIG. 2 is a cross sectional view illustrating the well formed in the microplate for use in the apparatus shown in FIG. 1;

FIGS. 4A and 4B show the enhanced horizontal line operator for use in the well edge detection;

FIG. 5 is a flow chart of detecting the pattern center;

FIG. 8 is a flow chart showing the judging operation;

FIGS. 12A to 12H are photographs representing various particle patterns; and

DESCRIPTION OF THE PREFERRED EMBODIMENTS

Figure 3A:
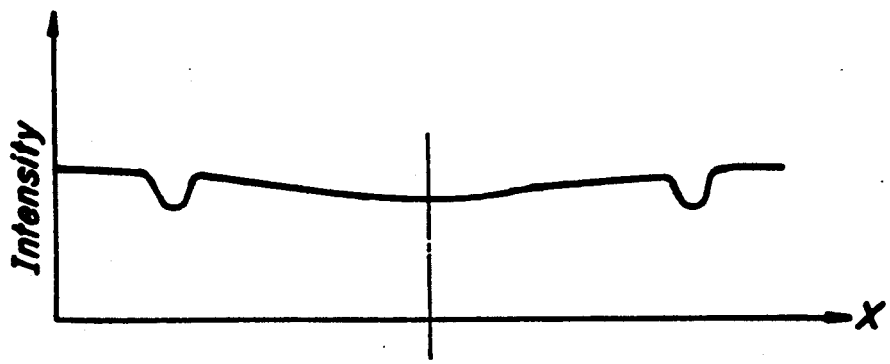
FIGS. 3A to 3D are signal waveforms for explaining the operation of detecting the well position.

FIG. 1 is a block diagram showing the construction of an embodiment of the apparatus for carrying out the method according to the invention. In the present embodiment, use is made of a microplate 1 in which a number of wells 2 serving as reaction vessels are formed in matrix. It should be noted that the method according to the invention is equally applicable to various kinds of reaction vessels other than the microplate. FIG. 2 is a cross section illustrating the well 2 formed in the top surface of the microplate 1. The well 2 has a conical bottom surface in which a number of fine steps are uniformly formed in order to form a basic layer of particles, said basic layer being particularly suitable for forming a stable agglutinated particle pattern. In the present embodiment, a diameter of the well 2 is 6 mm, and the microplate 1 is made of clear acrylic resin or glass. The inverted conically inclined base surface of the well 2 has a height of about 1.5 mm and is inclined at an angle of about 27° with respect to the horizontal plane. Each fine step formed in the conical base surface has the maximum depth of 2 to 50 μm and a length in the inclined direction of 5 to 200 μm. In the present embodiment, the image of the microplate 1 is picked up by a photoelectric image detecting device having a plurality of image sensors. The photoelectric image detecting device includes a plurality of solid state image sensors $3a$ to $3d$, a plurality of lenses $4a$ to $4d$ arranged in front of respective image sensors and an illumination lamp 5 arranged underneath the microplate 1. The microplate 1 is transported in a direction shown by an arrow A to effect a sub-scanning. A mechanism for driving the microplate 1 is well known in the art and does not relate to the subject matter of the present invention, so that it is not illustrated in FIG. 1. Further, various kinds of devices for supplying the microplate 1 onto a reaction line, delivering sample liquid and reagent liquids into the wells 2 and transporting the microplate along the reaction line are also not shown in FIG. 1. These devices may be those illustrated in the above mentioned U.S. Pat. No. 4,727,033. In the present embodiment, in order to pick-up the image of the microplate by the single sub-scanning, there are provided a plurality of the image sensors, each sensors picking up parts of the microplate image simultaneously.

The apparatus further comprises a switching circuit 6 for selecting photoelectrically converted image signals supplied from the image sensors $3a$ to $3d$ via preamplifiers $7a$ to $7d$, respectively. An image signal selected by the switching circuit 6 is supplied by means of an amplifier 8 to an analog-digital converter 9, and a converted digital image signal is stored in an image memory 10. The solid state image sensors $3a$ to $3d$ are driven by a driver circuit 11 which is controlled by a timing signal generator 12. The switching circuit 6, analog-digital converter 9 and memory 10 are also controlled by the timing signals supplied from the timing signal generator 12. The microplate 1 is driven in the direction A at a constant speed by a motor 13 which is energized by a motor driver 14. Further, the illumination lamp 5 comprising a fluorescent lamp is energized by a lamp power source 15. In order to operate the above mentioned circuit elements in conjunction with each other, there is provided a host processor unit 16. Further, in order to process the two-dimensional image data to judge the agglutination, the image data stored in the memory 10 is read out into a fast processor 17 which is coupled with the host processor unit 16 via an interface 18. In the host processor unit 16, at first the two-dimensional image data is processed to detect the boundary between the well 2 and the top surface of the microplate 1 to extract the image signal representing the particle pattern formed on the inclined bottom surface of the well, and then various kinds of pictorial characteristics of the particle patterns are derived and the particle pattern is judged on the basis of these characteristics.

Next, the operation of the host processor unit 16 will be explained in detail.

DETECTION OF WELL POSITION

Figure 3B:
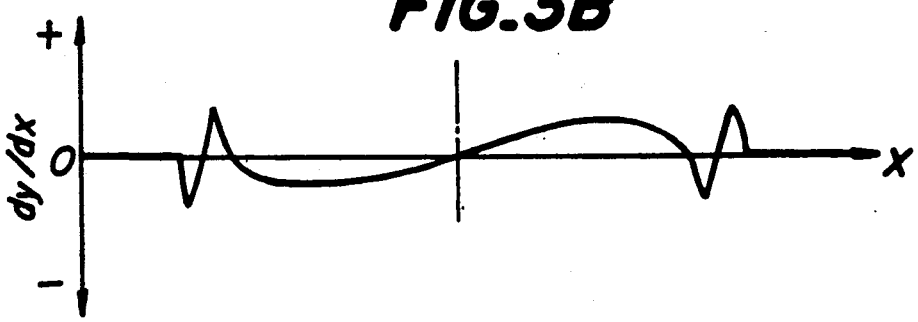
Figure 3C:
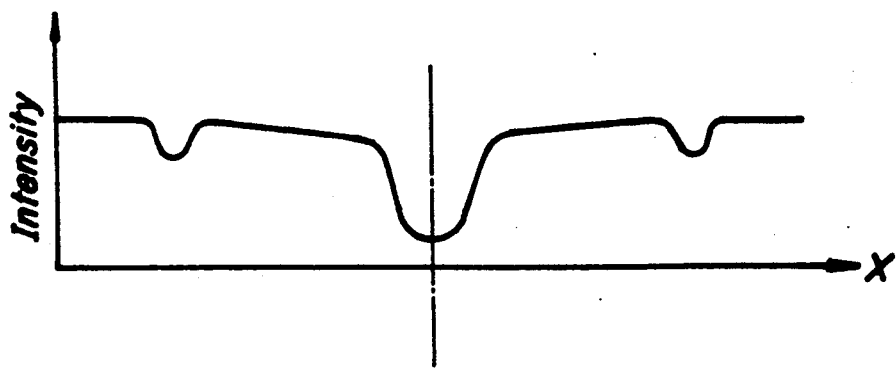
Figure 3D:
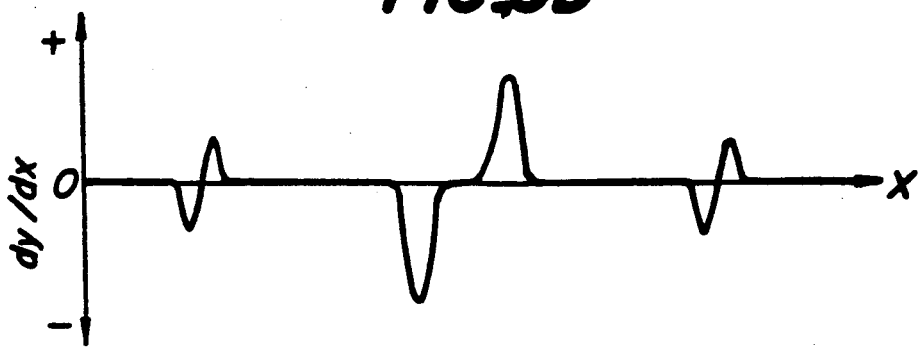

In the method according to the invention, it is not necessary to define the position of the wells 2 relative to the image pick-up device in a precise manner, because the position of the wells in the whole microplate image is detected by processing the two-dimensional image data. Therefore, the driving mechanism for moving the microplate 1 with respect to the image pick-up device can be made simple and inexpensive. In the present embodiment, the edge of the well 2 is first detected by deriving a two-dimensional first order derivation, i.e. convolution. To this end, various kinds of operators have been designed. The experiment has shown that an enhanced horizontal line 4 operator is the best one. FIG. 3A shows a light intensity profile along a diameter of the well 2, and FIG. 3B is a first derivation thereof for the typical agglutinated particle pattern, while FIGS. 3C and 3D represent the light intensity profile and the first derivation thereof for a typical non-agglutinated particle pattern. As be understood from FIGS. 3B and 3D, the first derivation $dy/dx$ becomes positive for a left side edge portion of the well and becomes negative for a right side edge portion of the well. By utilizing this fact, use may be made of an operator for detecting $dy/dx > 0$ for the left side edge portion of the well and an operator for detecting $dy/dx < 0$ for the right side edge portion of the well. In the present embodiment, in order to remove the high frequency noise component due to the averaging, use is made of the enhanced horizontal line 4 operator which is illustrated in FIGS. 4A and 4B for the left and right edge portions of the well, respectively.

Figure 6:
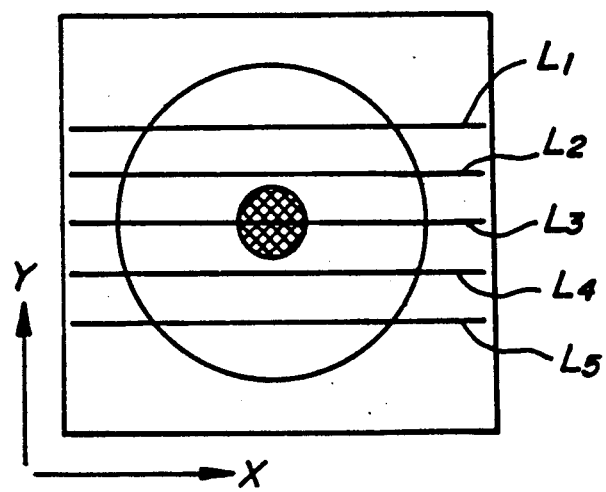
FIG. 6 represents the scanning lines for detecting the well edge.
Figure 7:
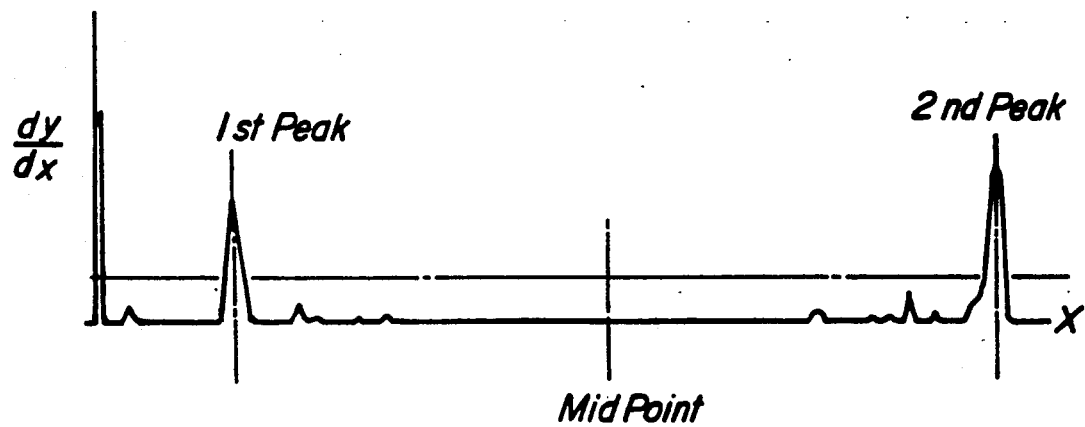
FIG. 7 denotes a signal waveform after being operated by the enhanced horizontal line 4 operator.

FIG. 5 is a flow chart for explaining the operation for detecting the horizontal well position. The two-dimensional image signal is first passed through a low pas filter and then is processed by the enhanced horizontal line 4 operators shown in FIGS. 4A and 4B for the left and right edge portions of the well, respectively. It should be noted that since the well 2 are arranged in the microplate 1 in a regular matrix form, rather large image areas including respective well images can be easily extracted from the whole two-dimensional image of the microplate 1. The same operation is repeated for successive five lines on of which passes through the center of the well bottom or a proximity thereof. FIG. 6 is a plan view showing the position of the five lines $L_1$ to $L_5$ relative to the well 2. It should be noted that if the number of the successive scanning lines are increased, the detecting accuracy becomes high but it takes much more time for processing the operator. Contrary thereto, if the number of the scanning lines are decreased, the detecting accuracy becomes low but the time for processing can be made short. FIG. 7 is a typical waveform of the operated signal along a line passing the center of the well bottom. Then, edges near both ends of each lines are detected as first and second peaks. Next, it is confirmed whether the detected peaks are affected by the noise component or not. This can be effected by comparing the derivation at the peak with a predetermined threshold value. If the value of the derivation is smaller than the threshold value, the detected peak is judged to be influenced by the noise and the relevant line is discarded. Further, a distance between the first and second peaks is calculated and then is compared with a predetermined threshold value. If the calculated distance between the first and second peaks is larger than 6.6 mm or smaller than 2.41 mm, it is judged that the edges of the well are not detected correctly. The well has its diameter of 6.0 mm. Further, the upper and lower limits of the distance between the first and second peaks are determined by taking the diameter of the well, the distance between successive scanning lines and the accuracy of the mechanism for driving the microplate 1 into consideration. In this manner, the edges of the well on the scanning line passing through the well are detected precisely. Next, a middle point between the first and second edges is calculated. The above operation is carried out for respective five lines. Then, it is confirmed whether or not the calculated middle points are within a predetermined range of $\pm 1.0$ mm. If a calculated middle point is beyond said range, the relevant line is discarded and a new line situated near the relevant line is selected. After the middle points of five lines situating the predetermined range have been calculated, an average thereof is derived as a detected center of the well. The above operation is performed in two orthogonal directions X and Y and the position of the well center in the two-dimensional image plane is determined.

EXTRACTION OF IMAGE CHARACTERISTICS

As explained above, in order to effect the judgment of the particle pattern in an efficient and prompt manner, it is advantageous to judge first the typical agglutinated and non-agglutinated patterns. In the present embodiment, these typical or true patterns are detected by utilizing the fact that the non-agglutinated particle pattern has a clear and sharp edge at a boundary of the center dot formed by a number of particles collected in the lowest portion of the conical bottom surface of the reaction vessel. When the particle pattern is visually judged with the naked eyes, the peripheral configuration of the center dot of the particle patterns is first examined. In the present embodiment, the same process is carried out for distinguishing the non-agglutinated pattern from the agglutinated pattern. When a pattern could not be judged to be the agglutinated one or the non-agglutinated one, the relevant pattern is further checked by using other characteristics.

Figure 9A:
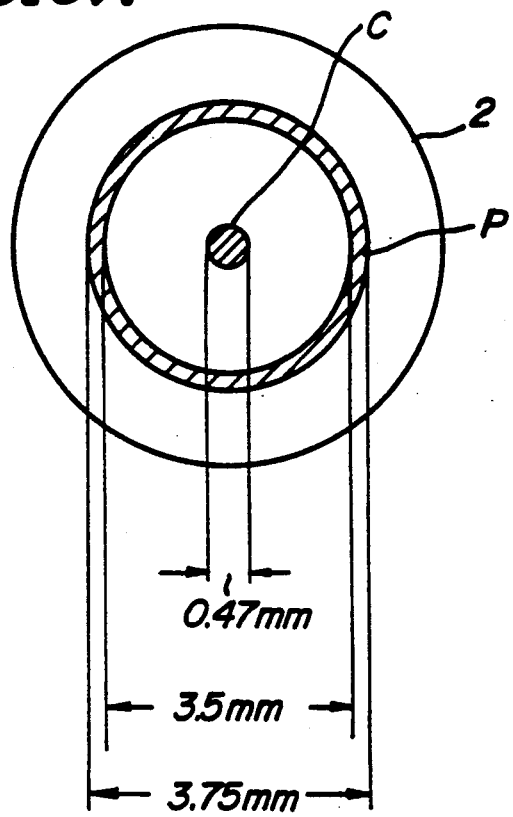
FIG. 9A is a plan view illustrating the central and peripheral portions of the bottom of the reaction vessel.
Figure 9B:
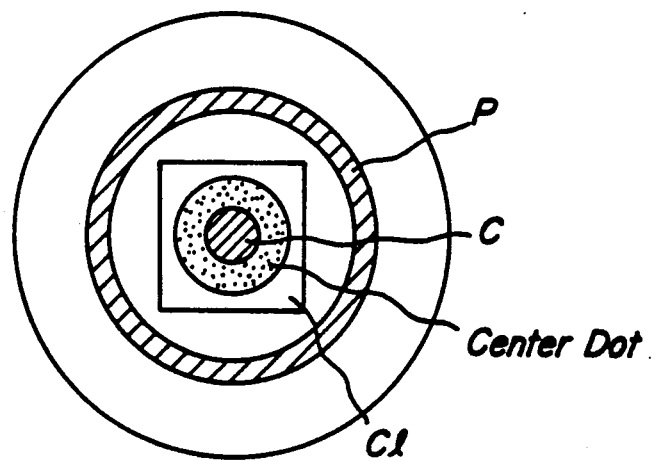
FIG. 9B is a plan view representing the rotation of these central and peripheral portions, and the region including the center dot of the typical non-agglutinated pattern.

FIG. 8 is a flow chart representing the judgment of the particle pattern by extracting the characteristics of the image of the particle pattern formed on the bottom surface of the reaction vessel 1. At first, in order to distinguish the blank sample from usual samples, a ratio of the intensity of the peripheral portion of the well to the intensity of the background area surrounding the well is calculated, and then the calculated ratio is compared with a predetermined threshold value. FIG. 9A is a plan view showing the peripheral portion P and the central portion C of the well 2 and FIG. 9B is a plan view explaining a relation in size and position among the center dot of the typical non-agglutinated pattern, the central portion C, the peripheral portion P and the region C including the central portion, which is used in SVC judgment explained in later. As is clear from FIG. 9B, the size of the central portion C is so determined as to be included in the center dot of the typical non-agglutinated pattern. If the size of central portion C is larger than the center dot of the typical non-agglutinated pattern, the high intensity part of the particle pattern surrounding the center dot is included in the central portion C, and thus, the average intensity of the center dot becomes high. Further the ratio of the average intensities of the center portion C to the peripheral portion P becomes so large that it becomes difficult to clearly discriminate the non-agglutinated pattern from the other pattern. To the contrary, if the size of the central portion C is too small, the signal representing the ratio $C_{AVE}/P$ becomes liable to be affected by noises caused by dust adhered on the center portion of the well or a clot formed in the particle pattern. Further, in a case that the center portion C is set too small, the ratio $C_{AVE}/P$ varies depending upon the situation of the center portion C in the center dot of the particle pattern. Therefore, it is also difficult to obtain the correct value of $C_{AVE}/P$. Taking the above-mentioned facts into consideration, the diameter of the central portion C is determined to be 0.47 mm in the present embodiment.

On the other hand, the intensity of the peripheral portion P is calculated as average intensities of pixels within the peripheral portion P. In order to shorten the data processing time for deriving the average intensity of the peripheral portion, the size of the circle of the peripheral portion P should be made small. However, if the size or area of the peripheral portion P is too small, the data processing thereof is not performed accurately due to the dust adhered on the peripheral portion of the well or the clot formed in the particle pattern. Moreover, the peripheral portion P should not have a directional property in shape. In other words, the peripheral portion P is desired to have a circular shape. The best position of the peripheral portion P is a middle position between the periphery of the center dot of the typical non-agglutinated pattern and the periphery of the well. If the peripheral portion P situates between the periphery of the center dot and the periphery of the well, even if the position of the well detected by the CCD is deviated from the actual position, the data processing for deriving the average intensity of the peripheral portion P can be effected correctly. Considering such conditions, the peripheral portion P is existed in a range between a circle having a diameter of 3.5 mm and a circle having a diameter of 3.75 mm in this embodiment. It should be noted that these circles are concentrical with the center point of the well bottom. When said ratio of the average intensity of the peripheral portion P to the average intensity of the background is greater than 0.9, it can be judged that the blank sample is detected, but when the ratio is equal to or smaller than 0.9, the detected pattern is judged to be the sample pattern. In this manner, the usual samples can be distinguished from the blank sample.

Figures 10A, 10B, 13:
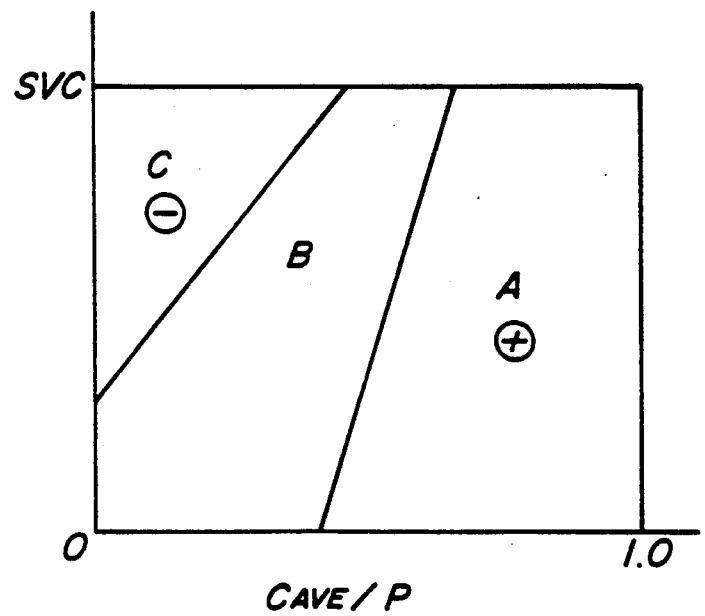
FIGS. 10A and 10B show the Sobel's operator for use in detecting the sharp boundary of the central dot of the pattern.
FIG. 13 is a graph showing an embodiment of the method according to the invention, in which a characteristic space is used for judging.
Figure 11A:
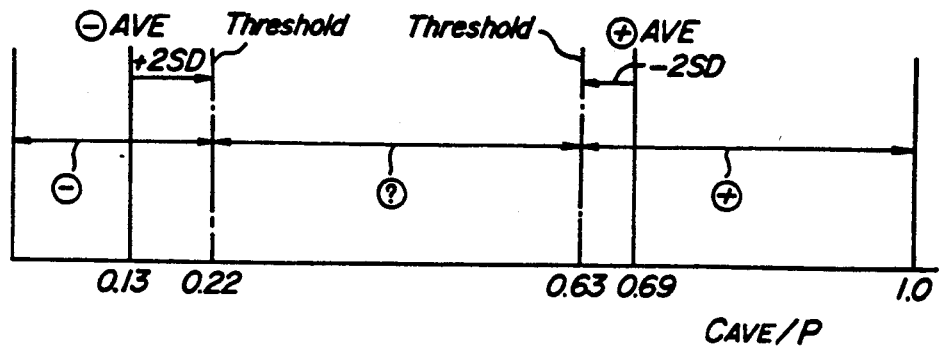
FIGS. 11A to 11D are graphs indicating the threshold values for judging the particle patterns to be agglutinated, non-agglutinated or uncertain.
Figure 11B:
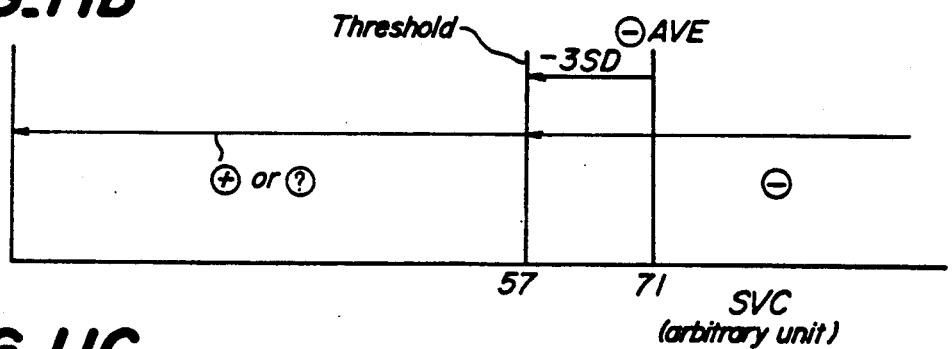

When the usual sample pattern is detected, then a ratio of the average intensity of the central portion C to the average intensity of the peripheral portion P is calculated and is compared with a predetermined threshold value to differentiate the typical or true agglutinated pattern from other patterns. However, it has been practically confirmed that it is sometimes difficult to correctly discriminate the typical or true agglutinated pattern from the true uncertained pattern. Therefore, in this embodiment, there are provided upper and lower threshold values in the judgment $C_{AVE}/P$. As shown in FIG. 11A when the ratio of $C_{AVE}/P$ is larger than the upper threshold value of 0.63, it is judged that the relevant particle pattern belongs to the agglutinated one, and when the ratio is smaller than the lower threshold value of 0.22, the relevant particle pattern is discriminated as the typical or true non-agglutinated pattern from the agglutinated pattern and the uncertained pattern. Further, when the ratio is between the upper and lower threshold values, the relevant particle pattern is judged at the time as an uncertain pattern and further processed. The average intensity of the central portion C may be calculated as an average of the intensities of pixels contained in the central portion C of the well. This judgment is called $C_{ave}/P$. At the same time, the first derivation of a part of the two-dimensional image situated within the region C1 which has a sufficient size for including the center dot of the particle pattern is calculated. In FIG. 9B, the region C1 having a rectangular shape is illustrated, but, the shape of the region is not limited to the rectangular one, but any desired shape can be applied thereto so far as the center dot is included in the region. This two-dimensional derivation can be carried out by using the so-called Sobel's operator. The Sobel's operator is illustrated in FIGS. 10A and 10B. The operator illustrated in FIG. 10A is to detect the sharp edge in the horizontal direction X and the operator of FIG. 10B is used to detect the sharp edge in the vertical direction Y. In the typical non-agglutinated pattern, there is produced a sharp edge at the periphery of the central dot in which a large number of particles are collected. Therefore, by using the Sobel's operator, it is possible to distinguish the typical non-agglutinated pattern from other patterns. When the two-dimensional derivation using the Sobel's operator exceeds a predetermined threshold value, the pattern is judged to be the non-agglutinated one. This judgment is termed as SVC. In this embodiment, when the two-dimensional derivation exceeds the upper threshold value 57, the relevant pattern is judged to be the non-agglutinated one as shown in FIG. 11B. In a modified embodiment of the method according to the present invention, upper and lower threshold values may be provided also in SVC judgment to classify the particle pattern into the agglutinated pattern, the non-agglutinated pattern, and the uncertained pattern, and the fast processing may be performed by the nine combinations of judgment results of SVC and $C_{AVE}/P$ each classified into the three regions.

As shown in FIG. 8, the result of the judgments are combined to determine the typical or true agglutinated particle pattern and the typical or true non-agglutinated pattern. That is to say, when a pattern is judged to be the agglutinated one by the judgments $C_{ave}/P$ and is judged to be the agglutinated one or the uncertain one by the judgment SVC, the relevant pattern is finally judged as the true agglutinated pattern, and when a pattern is discriminated as the non-agglutinated one by both the $C_{AVE}/P$ and SVC, the relevant pattern is finally judged as the true non-agglutinated pattern. It has been experimentally confirmed that almost all samples are judged as the true agglutinated and non-agglutinated patterns, and a very small number of patterns could not be classified as the uncertained patterns by the so far explained judgments. However, in case of testing the blood samples for use in the blood transportation, any ambiguity should be removed as far as possible. Therefore, in the present embodiment, particle patterns which have been judged by the above mentioned two judgments $C_{ave}/P$ and SVC in the contradictory manner are further processed.

Figure 11C:
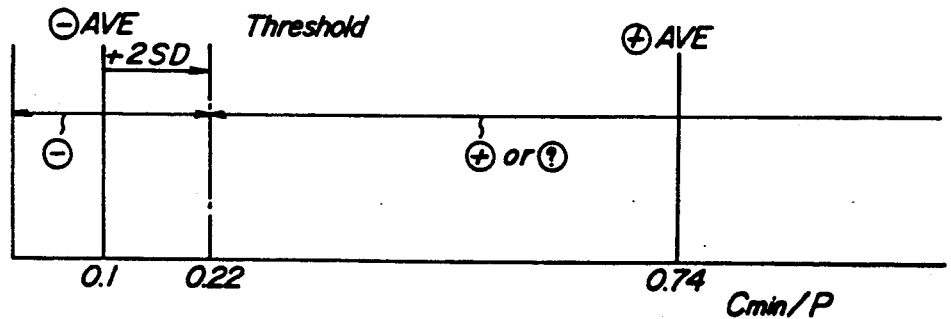
Figure 11D:
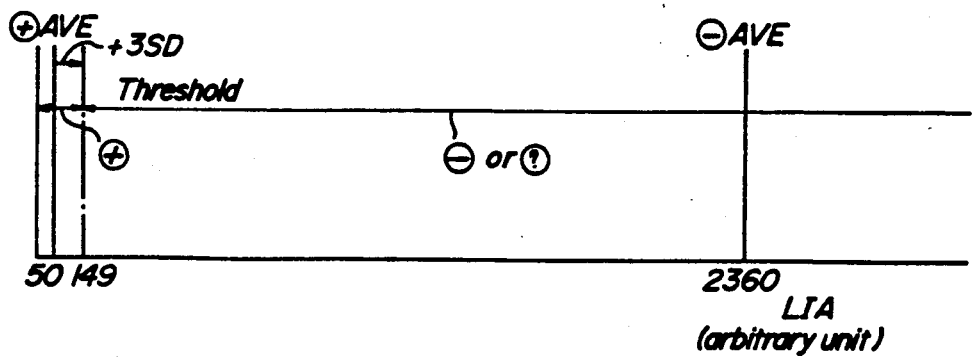

As illustrated in FIG. 8, the minimum value $C_{min}$ in the central portion C of the undetermined pattern is calculated and a ratio of the calculated minimum value $C_{min}$ to the average value of the peripheral portion P is compared with a predetermined threshold value. When this ratio is smaller than 0.22, the relevant pattern is preliminarily determined to be the non-agglutinated pattern as shown in FIG. 11C. This judgment is termed as $C_{min}/P$. The above mentioned judgment $C_{AVE}/P$ is effected by calculating the average intensities of the central/ portion C and the peripheral portion P. Therefore, when the center dot of the particle pattern is so small that the periphery of the center dot having a low intensity is included within the central portion C, when the particle pattern has a donut-like shape, i.e., the intensity of the center of the center dot is high, or when the position of the well is not aligned with the center of the central portion C, the actual intensity of the center portion C might not be reflected in the result of the judgment $C_{AVE}/P$. In these cases, the sample pattern is judged to be uncertain in the fast processing consisting of $C_{AVE}/P$ and SVC, and is further subjected to the $C_{min}/P$ judgment by which the intensity of the center dot can be measured correctly. However, the $C_{min}/P$ judgment has a tendency of being affected by noise, and therefore, the judgment $C_{AVE}/P$ is effected prior to the judgment $C_{min}/P$. At the same time, an area of the center dot having the intensity lower than a predetermined intensity is calculated and the calculated area is compared with a predetermined threshold value. The area of the center dot is defined by the following manner. The average intensity of the peripheral portion P is measured and a half value thereof is set as the threshold value (the contour of the center dot). The area having the intensity smaller than the threshold value is defined as a center dot. When the area of the center dot is smaller than the threshold value 149, the particle pattern is judged as the agglutinated one as illustrated in FIG. 11D. This judgment is called LIA for Low Intensity Area. Then, the result of the judgments $C_{min}/P$, LIA and SVC are combined, and only patterns which have been judged as the agglutinated pattern or the uncertain pattern by the judgments SVC and $C_{min}/P$ and judged as the agglutinated pattern by the judgment LIA are finally judged as the true agglutinated pattern, and the remaining patterns are finally judged as uncertain patterns which require the visual inspection or the reexamination.

In FIGS. 11A through 11D, there are indicated the average intensities of the agglutinated particle patterns and the average intensities of the non-agglutinated particle patterns and the threshold values for determining the particle patterns to be agglutinated, non agglutinated or uncertain one for each parameters, $C_{AVE}/P$, SVC, $C_{min}/P$ and LIA.

The inventors have conducted various experiments and found that the method according to the invention is superior to the known method. Now some experiments will be explained hereinbelow.

FIGS. 12A to 12H are photographs showing particle patterns of several samples. In these photographs, numbers in right lower corners denote the sample number. The following table represents the result of the judgment by the method according to the invention, the known method described in the aforementioned U.S. Pat. No. 4,727,033 and the visual judgment. In the table, the mark ±represents that the pattern is arbitrarily judged as the agglutinated pattern, the non-agglutinated pattern or the uncertain pattern depending on respective operators.

TABLE

| | Sample No. | | | | | | | |
|---|---|---|---|---|---|---|---|---|
| | 506 | 509 | 511 | 504 | 512 | 514 | 505 | 517 |
| Novel method of invention | | | | | | | | |
| $C_{AVE}/P$ | + | + | + | + | − | − | − | − |
| SVC | + | + | + | + | + | + | − | − |
| $C_{min}/P$ | | | | | − | − | | |
| LIA | | | | | − | − | | |
| Final judge | + | + | + | + | ? | ? | − | − |
| Visual judgement | + | + | + | + | ± | ± | − | − |
| Known method | + | ? | ? | ? | ? | − | − | − |

In the method according to the invention, samples Nos. 506, 509, 511 and 504 are judged to be the agglutinated pattern by both the judgments $C_{AVE}/P$ and SVC, so that these samples are finally judged as the true agglutination sample. Similarly, samples Nos. 505 and 517 are judged to belong to the non-agglutinated pattern by the judgments $C_{AVE}/P$ and SVC, so that these samples ar finally judged as the true non-agglutination sample. In the table, the agglutination is represented by + and the non-agglutination is denoted by −, while the uncertain condition is represented by ? mark. Two samples Nos. 512 and 514 are judged in the contradicting manner by the judgments $C_{AVE}/P$ and SVC, so that these samples are further subjected to the judgments $C_{min}/P$ and LIA. In these judgments, these samples are judged to be the non-agglutination, so that these samples are finally determined to be uncertain samples. This judgment result by the method according to the invention is identical with the result of the visual judgment. However, in the known method, the samples 509, 511 and 504 could not be definitely judged, and are classified as uncertain samples. Further, the sample No. 514 is erroneously judged to be the non-agglutination sample. From the experiment it has been confirmed that in the method according to the present invention, the judgment result which is substantially identical with that of the visual judgment can be obtained, the number of samples to be tested again, i.e. the reexamination rate can be reduced remarkably, and the possibility of the erroneous judgment can be decreased to a large extent.

The inventors have further experimentally confirmed that in the method according to the invention a ratio of samples which are subjected to the reexamination to the total number of samples can be reduced less than one percent, while ratios of samples, which are judged to be uncertain in respective judgments, to the total number of samples amount to about ten percent.

Further, in the method according to the invention, since the judgment is effected by processing the two-dimensional image data of the particle pattern and the final judgment is given by processing the image signal by at least two judgments, the particle pattern can be accurately and reliably judged even if the abnormal conditions such that a part of the particle pattern is peeled off the bottom surface of the reaction vessel, the center dot is very small, the center dot has the donut shape, the center dot is vague, etc. are recognized in the particle patterns.

The present invention is not limited to the embodiment explained above, but various alternations and modifications are conceived by those skilled in the art without departing from the scope of the invention. For instance, in FIG. 8, the judgment result of the fast processing is effected by means of combination of parameters, $C_{AVE}/P$ and SVC. That is to say, when a pattern is judged to be the agglutinated one by the judgment of $C_{AVE}/P$ and is judged to be the agglutinated one or the uncertain one by the judgment of SVC, it is judged that the relevant pattern is the true agglutinated one, and when a pattern is discriminated as the non-agglutinated one by both the judgments, the relevant pattern is judged as the real non-agglutinated one. Further, when the results of both the judgments cannot be applicable to these cases, the relevant particle pattern is judged as uncertain. However, it is possible to discriminate the particle pattern by taking the relative relation between the parameters into judgment, i.e. by using a characteristic space. In the characteristic space, there are plotted each parameters such as $C_{AVE}/P$, SVC, $C_{min}/P$ and LIA in co-ordinate axes. FIG. 13 is a graph showing an embodiment of a characteristic space in which the parameter SVC is plotted on the ordinate and the parameter $C_{AVE}/P$ on the abscissa. In this characteristic space, there are provided three domains A, B and C and when the characteristic of the particle patter determined by the value of SVC and $C_{AVE}/P$ is positioned in the domain A, the relevant pattern is judged to be the agglutinated pattern, and when the characteristic is situated in the domain C, the relevant pattern is judged to be the non-agglutinated pattern. Further, the characteristic is put in the domain B, the relevant pattern is judged to be uncertain and such particle patterns are analyzed visually with naked eyes or tested again. It should be noted that two or more parameters can be used to constitute a multi-dimensional characteristic space. It should be noted that the characteristic space may also be used in the final judgment of the particle pattern in which it is desired to judge the pattern more precisely.

What is claimed is:

1. A method of judging a particle pattern formed on an inclined bottom surface of a reaction vessel, said reaction vessel being formed in a microplate having a plurality of reaction vessels formed therein in a matrix, said method comprising the steps of:
   photoelectrically scanning an entire image of said microplate via a plurality of solid state image sensors to derive an image signal representing a two-dimensional image including the entirety of the particle pattern formed in said reaction vessel;
   storing image signals supplied from said solid state image sensors in a memory;
   detecting a pair of edge positions of said reaction vessel for each of a plurality of scanning lines passing across said reaction vessel with the aid of a first operator;
   calculating a plurality of middle points of detected plural pairs of edge positions of said reaction vessel;
   determining a center position of said reaction vessel by deriving an average of said plurality of middle points as a position signal;
   processing said image signal of the two-dimensional image on the basis of said position signal to derive at least two characteristics of the particle pattern; and
   judging the particle pattern on the basis of said at least two characteristics.

2. A method according to claim 1, further comprising a step of discriminating the particle pattern from a blank sample prior to judging the particle pattern.

3. A method according to claim 2, wherein said discriminating step comprises:
    deriving a first ratio of an average intensity of a peripheral portion of said reaction vessel to an average intensity of a background surrounding said reaction vessel; and
    comparing said first ratio with a predetermined first threshold value to judge that the pattern is of the blank sample when the first ratio is larger than the first threshold value.

4. A method according to claim 1, wherein prior to calculating a middle point from a pair of edge positions on a scanning line, a distance between these edge positions is calculated, and when the distance between these edge positions exceeds a predetermined threshold value, the relevant pair of edge positions is discarded.

5. A method according to claim 4, wherein prior to calculating the average of a plurality of middle points, each of the middle points is compared with a predetermined range, and when a middle point is not situated in said range, the relevant middle point is discarded.

6. A method according to claim 1, wherein said first operator is formed by an Enhanced Horizontal Line 4 Operator.

7. A method according to claim 1, wherein said particle pattern is first processed by a preliminary set of fast judgments to distinguish typical agglutinated and non-agglutinated patterns, and then the particle pattern is processed by a secondary set of precise judgments only when the particle pattern is not definitely judged by the preliminary set of fast judgments.

8. A method according to claim 7, wherein said preliminary set of fast judgments includes the steps of:
    deriving a first ratio of an average intensity of a central portion of the particle pattern to an average intensity of a peripheral portion thereof;
    comparing the first ratio with at least one predetermined first threshold value to judge that the particle pattern is an agglutinated pattern only when said first ratio is larger than said predetermined first threshold value;
    deriving a sharpness signal representing the sharpness of a boundary of a center dot formed by a number of particles collected in a lowest center portion of said reaction vessel;
    comparing said sharpness signal with at least one predetermined second threshold value to judge the particle pattern is a non-agglutinated pattern when the sharpness signal is larger than said second threshold value; and
    judging the particle pattern to be agglutinated or non-agglutinated only when the results of said two comparisons are consistent with each other.

9. A method according to claim 8, wherein said secondary set of precise judgments comprises:
    deriving a second ratio of a minimum intensity within said central portion to said average intensity of said peripheral portion;
    comparing said second ratio with a predetermined third threshold value to judge that the particle pattern is agglutinated when said second ratio is larger than said third threshold value;
    deriving an area of said center dot of the particle pattern;
    comparing said area of said center dot with a predetermined fourth threshold value to judge that the particle pattern is agglutinated when said area is smaller than said fourth threshold value; and
    judging the particle pattern to be a true agglutinated pattern only when the results of said two comparisons indicate that the relevant particle pattern is agglutinated.

10. A method according to claim 1, wherein said step of judging the particle pattern is effected by detecting a position of the particle pattern in a characteristic space composed of at least two characteristics of the particle pattern.

* * * * *